(12) United States Patent
Böhm et al.

(10) Patent No.: US 11,028,357 B2
(45) Date of Patent: Jun. 8, 2021

(54) SYSTEM FOR ANALYZING AND SORTING OF PETRI DISHES

(71) Applicant: CLEVER CULTURE SYSTEMS AG, Bach (CH)

(72) Inventors: Alexander Böhm, Klagenfurt am Wörthersee (AT); Nedim Bogilovic, Klagenfurt am Wörthersee (AT); Wolfgang Stiegmaier, Zeltweg (AT)

(73) Assignee: Clever Culture Systems AG, Bäch (CH)

( * ) Notice: Subject to any disclaimer, the term of this patent is extended or adjusted under 35 U.S.C. 154(b) by 336 days.

(21) Appl. No.: 16/091,430

(22) PCT Filed: Mar. 13, 2017

(86) PCT No.: PCT/EP2017/055788
§ 371 (c)(1),
(2) Date: Oct. 4, 2018

(87) PCT Pub. No.: WO2017/174299
PCT Pub. Date: Oct. 12, 2017

(65) Prior Publication Data
US 2019/0153374 A1   May 23, 2019

(30) Foreign Application Priority Data
Apr. 4, 2016  (EP) .................................... 16163702

(51) Int. Cl.
*C12M 1/22* (2006.01)
*C12M 1/00* (2006.01)
(Continued)

(52) U.S. Cl.
CPC ............ *C12M 23/10* (2013.01); *C12M 23/48* (2013.01); *C12M 23/50* (2013.01); *C12M 41/48* (2013.01);
(Continued)

(58) Field of Classification Search
None
See application file for complete search history.

(56) References Cited

U.S. PATENT DOCUMENTS

2012/0251275 A1* 10/2012 Malin ................ G01N 35/0099
414/225.01
2014/0030802 A1   1/2014 Eberle et al.

FOREIGN PATENT DOCUMENTS

EP        2 482 079        8/2012

OTHER PUBLICATIONS

PCT/EP2017/055788, Apr. 4, 2017, International Search Report and Written Opinion.

* cited by examiner

*Primary Examiner* — Matthew D Krcha
(74) *Attorney, Agent, or Firm* — Workman Nydegger

(57) ABSTRACT

A system for analyzing and sorting of petri dishes comprising an analysis tool, a control unit, a first elevator movable along a first elevator axis, a conveyor with a conveyor plane, and at least one carrier built to carry the petri dishes along a carrier axis.

The analysis tool is built to assign information to the petri dish, and in case of a first information assigned to the petri dish the control unit is built to move the first elevator into a carrier position, wherein, as soon as the first elevator reaches the carrier position, the control unit is built to move a substantially flat first plate along the first elevator axis from a first neutral position located in the conveyor plane into a first transfer position.

15 Claims, 3 Drawing Sheets

(51) Int. Cl.
*C12M 1/36* (2006.01)
*C12M 3/00* (2006.01)
*G01N 35/00* (2006.01)
*G01N 35/04* (2006.01)

(52) U.S. Cl.
CPC . *G01N 35/0099* (2013.01); *G01N 2035/0425* (2013.01)

SYSTEM FOR ANALYZING AND SORTING OF PETRI DISHES

The present invention is related to a system for analyzing and sorting of petri dishes comprising an analysis tool, a control unit built to communicate with the analysis tool, a first elevator movable along a first elevator axis by the control unit, a conveyor with a conveyor plane substantially rectangular to the first elevator axis, and at least one carrier built to carry the petri dishes along a carrier axis substantially parallel to the first elevator axis.

The present invention is furthermore related to a method for analyzing and sorting of petri dishes with a system comprising an analysis tool, a control unit, a first elevator movable along a first elevator axis, a conveyor, and at least one carrier and at least one multi-carrier, respectively built to carry the petri dishes.

Petri dishes are flat, circular and transparent containers with an overlapping lid used in biology, medicine or chemistry for the cultivation of microorganisms and cell cultures. A shallow layer of gel growth medium applied onto the bottom of the container supplies the microorganisms with water and nutrients. In general, petri dishes are stored and handled with the lid down and the container upwards in order to improve the closure between the lid and the container and to accumulate excess water in the lid. During an incubation period or an analysis of the cell cultures, these cultures need to be frequently optically inspected. Thus, there is a high need for process automation, especially regarding handling and optical inspection of petri dishes.

EP 2 482 079 A2 discloses a system for analyzing and handling of petri dishes. The system comprises a storage chamber and two handling systems that via a transfer position transfer samples from the storage chamber to an analysis tool and from the analysis tool back into the storage chamber. The system further comprises a transport system that allows to input/output single petri dishes into/from the storage chamber.

This known system has the disadvantage that the handling of petri dishes is very complex and thus slow. In addition, the transport system for the input and output of petri dishes allows only to manually put petri dishes into the system or take out petri dishes from the system one by one, whereas the system does not offer any automated sorting of the analyzed samples. As a consequence, especially if a high number of petri dishes needs to be analyzed and sorted within a short time, working with this known system may be cumbersome and prone to mistakes.

Consequently, it is an objective of the presented invention to provide an improved system for analyzing and sorting of petri dishes that saves time and reduces the error-proneness, and that allows to handle and sort petri dishes in a very fast, simple and safe way.

This objective is achieved with a system comprising the analysis tool, which is built to assign information to the petri dish, and the control unit, which is built to move the first elevator along a conveyor direction of the conveyor, and that in case of a first information assigned to the petri dish the control unit is built to move the first elevator into a carrier position, which is reached as soon as the carrier axis and the first elevator axis substantially coincide, wherein, as soon as the first elevator reaches the carrier position, the control unit is built to move a substantially flat first plate of the first elevator along the first elevator axis, which first plate is built to receive the petri dish, in order to move the first plate from a first neutral position located in the conveyor plane into a first transfer position, which is reached as soon as the petri dish is being taken over by the at least one carrier.

It is furthermore an objective of the presented invention to provide a method for analyzing and sorting of petri dishes that allows to handle and sort petri dishes in a very fast, simple and safe way.

This objective is achieved with a method that comprises the following steps:

Assign information to the petri dish analyzed by the analysis tool and communicate this information to the control unit;

receive the petri dish on a substantially flat first plate of the first elevator;

in case of a first information assigned to the petri dish move the first elevator along a conveyor direction of the conveyor into a carrier position and, as soon as the first elevator reaches the carrier position, move the first plate along the first elevator axis from a first neutral position into a first transfer position, and take-over the petri dish by the carrier.

The system according to the invention comprises the advantage that petri dishes of advantageously circular form and basically any size can be analyzed and sorted in a very fast, safe and simple way. Since the first elevator comprises the substantially flat first plate to receive the petri dishes, a recently analyzed petri dish can be simply pushed onto the first plate without the need for extra lifting or lowering the petri dish. The analysis tool is advantageously built to assign information to the petri dish, for example information regarding an analysis result. According to this result, the control unit is built to move the first elevator into the carrier position, and to move the flat first plate with the petri dish into the corresponding carrier. Advantageously, in an installation orientation of the system, this carrier is positioned directly above the conveyor. Hereby, the control unit can simply move the first plate from the first neutral position upwards into the first transfer position, wherein the petri dish is automatically being taken over by the carrier.

Advantageously, the system according to the invention comprises more than one carrier along the conveyor, for example four carriers, wherein every carrier may be related to a certain assigned information of the petri dish. Consequently, the advantage is given that the system can automatically sort and transfer every analyzed petri dish to its corresponding carrier.

In an advantageous embodiment according to the invention, the first elevator comprises pushing means built to move the petri dish on the conveyor plane along a pushing axis substantially transversal to the conveyor direction. Thus, in case of a second information assigned to the petri dish the control unit is built to move the first elevator into a multi-carrier position, wherein, as soon as the first elevator reaches the multi-carrier position, the control unit is built to control the pushing means to move the petri dish along the pushing axis onto a second plate of a second elevator or onto a prior petri dish carried by the second plate, which second plate is movable along a second elevator axis by the control unit. Thus, the system has more sorting options.

Advantageously, the second elevator comprises a sensor built to communicate with the control unit and to detect the petri dish on the second elevator in order to automatically start the movement of the second elevator as soon as a petri dish is being received by the second plate.

In a further advantageous embodiment, the system comprises at least one multi-carrier built to carry the petri dishes along at least two carrier axes substantially parallel to the second elevator axis, wherein one carrier axis substantially coincides with the second elevator axis, and wherein the control unit is built to move the second plate along the second elevator axis from a second neutral position located in the conveyor plane downwards into second transfer positions, which are reached each time the bottom container of the upmost petri dish carried by the second plate levels with the conveyor plane. Hereby, the advantage is given that the system can handle a higher number of petri dishes, since the multi-carrier enables to carry more petri dishes than the carrier. In addition, sorting can be split into two planes, namely an upper plane, above the conveyor, comprising one or more carriers and a lower plane, below the conveyor, comprising one or more multi-carriers. Hereby the advantage is given that for example different petri dishes with a different assigned information can be clearly separated in order to enhance the sorting effect and reduce the risk of mistakes. For example, petri dishes with an "expected" analysis result may automatically be sorted into one of the multi-carriers below the conveyor, and petri dishes with an "unexpected" analysis result may automatically be sorted into one of the carriers above the conveyor.

Advantageously, the multi-carrier is built to carry the petri dishes along four carrier axes in order to carry more petri dishes at one time. Hereby, in an advantageous embodiment the system may comprise at least one rotatable platform built to receive the at least one multi-carrier, wherein the rotatable platform is rotatable around a platform axis by the control unit in order to position the carrier axes in accordance to the second elevator axis. Thus, the multi-carrier can automatically be rotated by the system, and an empty multi-carrier capacity along a carrier axis can be positioned in accordance to the second elevator axis up as soon as the multi-carrier capacity along a previous carrier axis is used up.

In a further advantageous embodiment, the system comprises a carrier sensor system built to communicate with the control unit and to detect the petri dishes carried by the at least one carrier or the at least one multi-carrier. Hereby, the advantage is given that the control unit and the system exactly know at each point in time, which carrier carries how many samples and if every sample is in its correct position within the carrier.

These and further advantageous embodiments of the invention will be explained based on the following description and the accompanying drawings. The person skilled in the art will understand that various embodiments may be combined.

Figure 1:
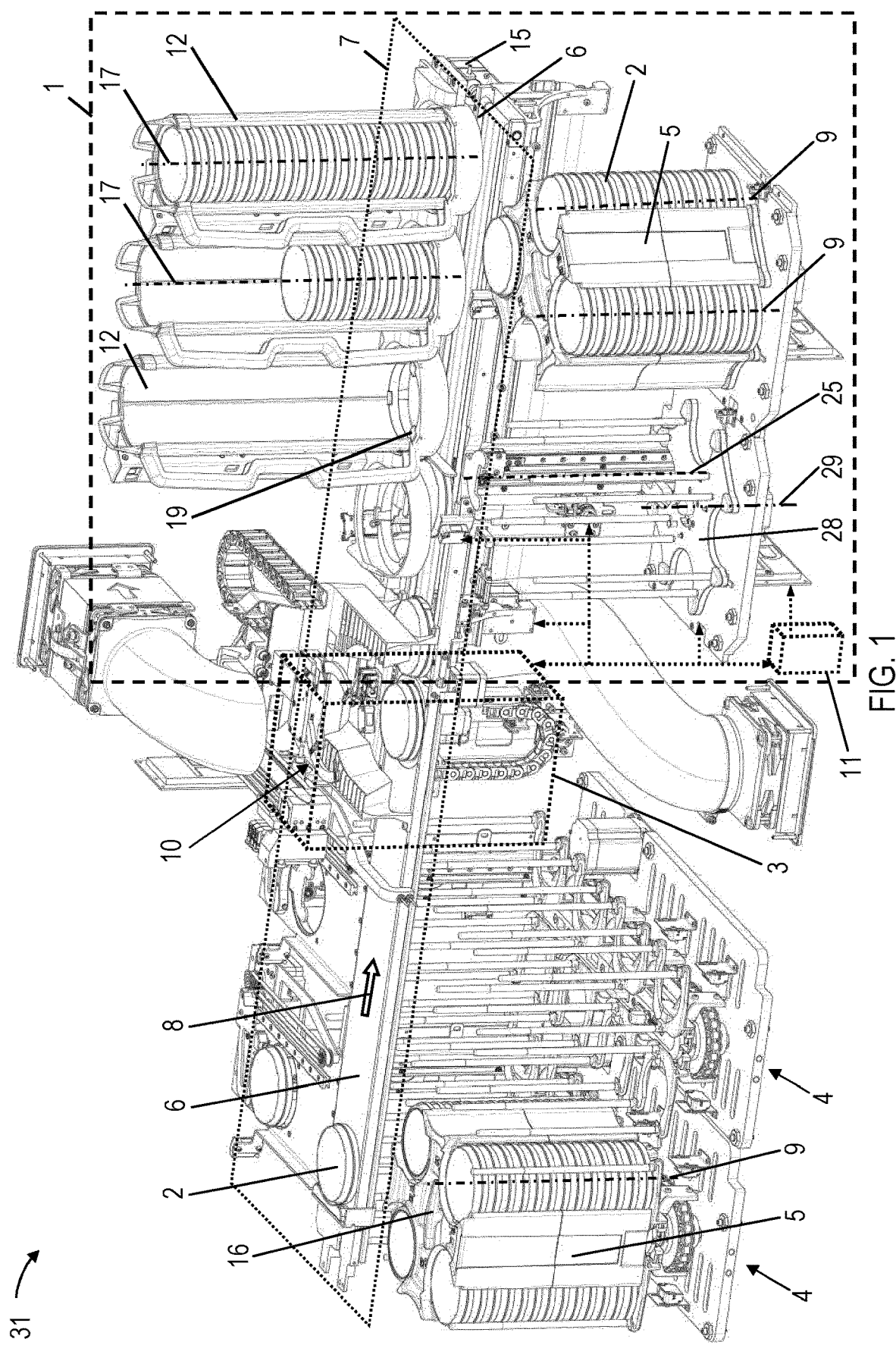
FIG. 1 shows in a perspective view a processing apparatus for fully automated handling, analysis and sub-sequent sorting of petri dishes.

FIG. 1 shows a processing apparatus 31 for fully automated handling, analysis and sub-sequent sorting of petri dishes 2. The analysis and sub-sequent sorting may be performed by a system 1 for analyzing and sorting of petri dishes 2 comprising an analysis tool 3. This analysis tool 3 may be an optical analysis tool, such as an automated microscope. The processing apparatus 31 comprises two input systems 4 for automatically supplying the petri dishes 2, wherein these input systems 4 are compatible with a multi-carrier 5.

Each multi-carrier 5 comprises four multi-carrier axes 9 in order to carry stacks of petri dishes 2 along these multi-carrier axes 9. Thus, the multi-carrier 5 can be conveniently handled by a handle 16 situated substantially along a central axis of the multi-carrier 5. Each multi-carrier 5 is received by a rotatable platform 28, wherein the rotatable platform 28 is rotatable around a platform axis 29. Thus, the multi-carriers 5 can automatically be rotated in order to position a new, "empty" multi-carrier axis 9 in accordance to a second elevator axis 25 of a second elevator 24, as soon as the capacity of the previous multi-carrier axis 9 is used up. The multi-carriers 5 may for example be used to receive petri dishes 2 with an "expected" analysis result. "To position a multi-carrier axis 9 in accordance to a second elevator axis 25" in this context means that the respective multi-carrier axis 9 substantially coincides with the second elevator axis 25 in order to take over and carry the petri dishes 2, as being described below.

A conveyor 6 connects the input systems 4 with the system 1 for analyzing and sorting of petri dishes 2, wherein a central transfer and handling system 10 automatically transfers the petri dishes 2 into and out of the analysis tool 3. Hereby, the petri dishes 2 are moved on a conveyor plane 7 along a conveyor direction 8 of the conveyor 6. This movement can for example be performed by fully automated pushing means or a conveyor drive 15.

The processing apparatus 31 for fully automated handling, analysis and sub-sequent sorting of petri dishes 2 according to the invention has the advantage that the petri dishes 2 are moved on the conveyor plane 7 along the conveyor direction 8 all the way through the processing apparatus 31. Only during analysis the petri dishes 2 may be lifted up and transferred into the analysis tool 3, which may for example be situated in front of the processing apparatus 31, as indicated in FIG. 1. As a consequence, automated handling, analysis and sub-sequent sorting of petri dishes 2 can be done faster and safer as compared to other comparable, commercially available systems.

The petri dishes 2 are advantageously of cylindrical form, involving a cylindrical bottom container and a cylindrical lid. The petri dishes 2 are handled with the lid down and the bottom container upwards throughout the whole processing apparatus 31 and system 1. Of course, the processing apparatus 31 and the system 1 can also handle the petri dishes 2 with the bottom container down and the lid upwards.

Figure 2:
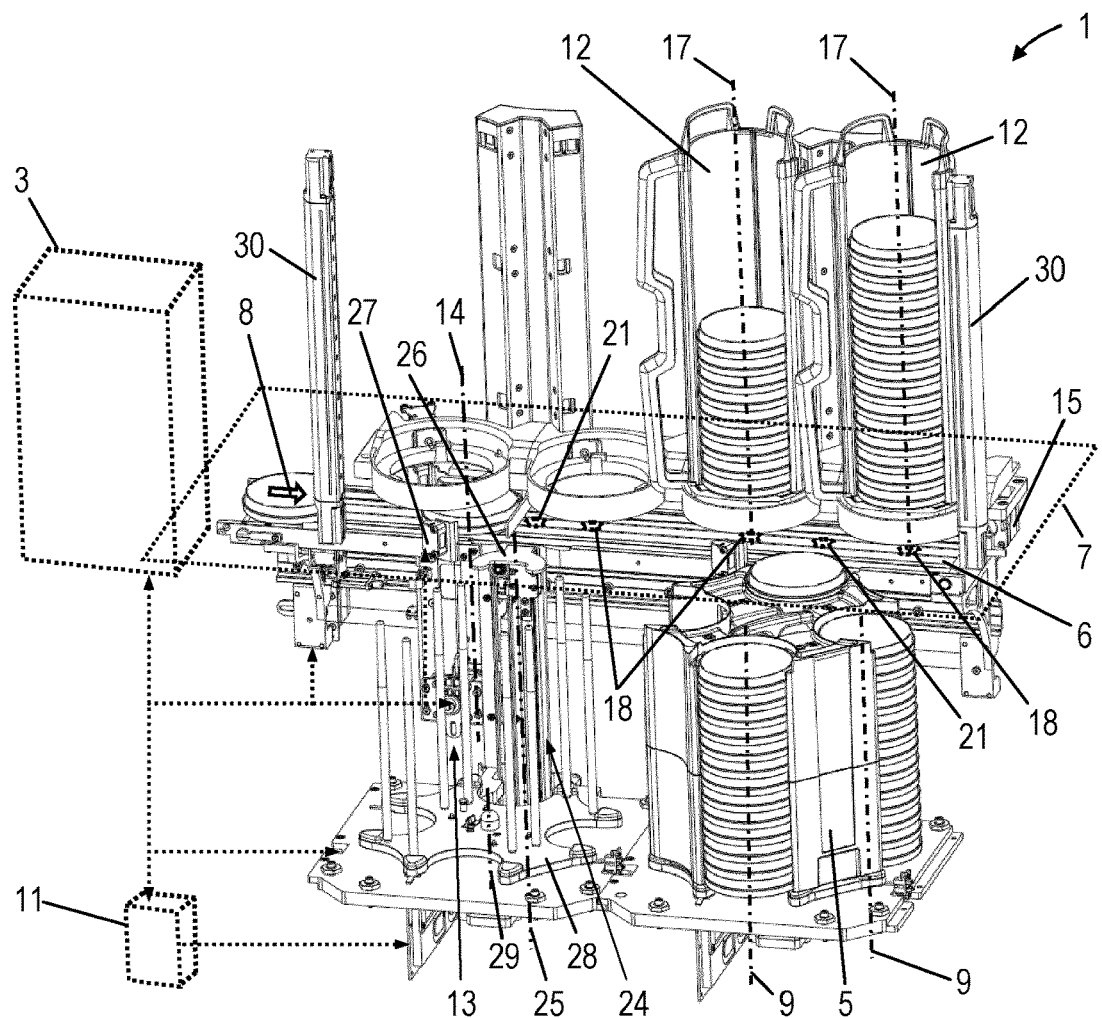
FIG. 2 shows in a perspective view a system for analyzing and sorting of petri dishes according to a first embodiment of the invention.

The system 1 for analyzing and sorting of petri dishes 2 according to a first embodiment is shown in FIG. 2. Besides the analysis tool 3, the system 1 comprises a control unit 11 built to communicate with the analysis tool 3, a first elevator 13 with a first elevator axis 14, which is substantially rectangular to the conveyor plane 7, the second elevator 24 with the second elevator axis 25, which is substantially rectangular to the conveyor plane 7, and four carriers 12, wherein only two carriers are shown in FIG. 2. The system 1 further comprises a carrier sensor system built to communicate with the control unit 11 and to detect the petri dishes 2 carried by the carriers 12. Each column 30 of the sensor system may for example transmit and receive a grid of parallel laser beams interfering with the petri dishes 2 carried by the carriers 12. Those skilled in the art will be aware of the fact that other technical solutions of such a sensor system may be used.

In the present first embodiment, the part of the conveyor 6 corresponding to the system 1 is realized as a conveyor belt driven by the conveyor drive 15, which is controlled by the control unit 11. Thus, the first elevator 13 can be moved along the conveyor direction 8 by the control unit 11. In addition, the conveyor belt is split into two conveyor belts 32 separated by a gap in order that the first elevator 13 can be moved along the first elevator axis 14. Alternatively, the conveyor 6 could be realized as a pair of guiding rails guiding electrically driven wheels of the first elevator 13, which wheels are driven by the control unit 11. Alternatively, the conveyor or the pair of guiding rails could comprise a belt or a chain drive connected to the first elevator 13, or the first elevator 13 could optionally be moved in a suspended configuration. Those skilled in the art will be aware of the fact that other configurations and drive mechanisms of the conveyor 6 may be used.

Each carrier 12 is built to carry the petri dishes 2 along a carrier axis 17 substantially parallel to the first elevator axis 14. The carriers 12 are smaller and lighter than the multi-carriers 5 and can be handled more easily and faster as compared to the multi-carriers 5. Such carriers 12 may for example be used to receive petri dishes 2 with an "unexpected" analysis result that needs to be re-analyzed by a skilled person or another analysis tool. Alternatively, these carriers 12 may be used to receive petri dishes 2 with a "certain" analysis result or a "certain" assigned information, wherein the corresponding carrier 12 comprises a corresponding marking, such as a colour code, a bar code, a number code or any other comparable labelling.

Figure 3:
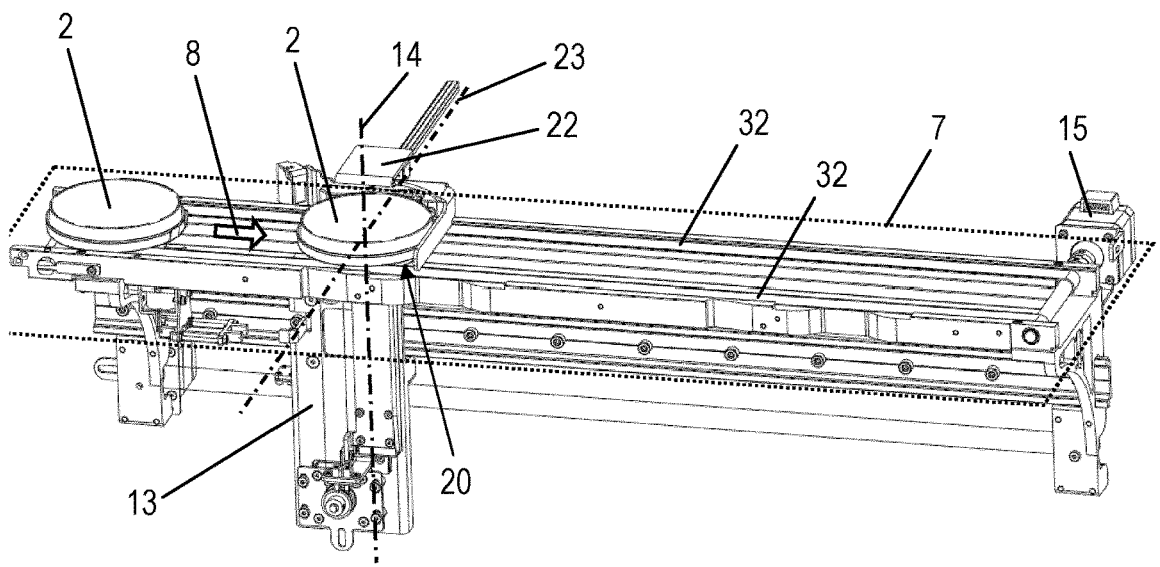
FIG. 3 shows in a perspective view from above a part of the system of FIG. 2.
Figure 4:
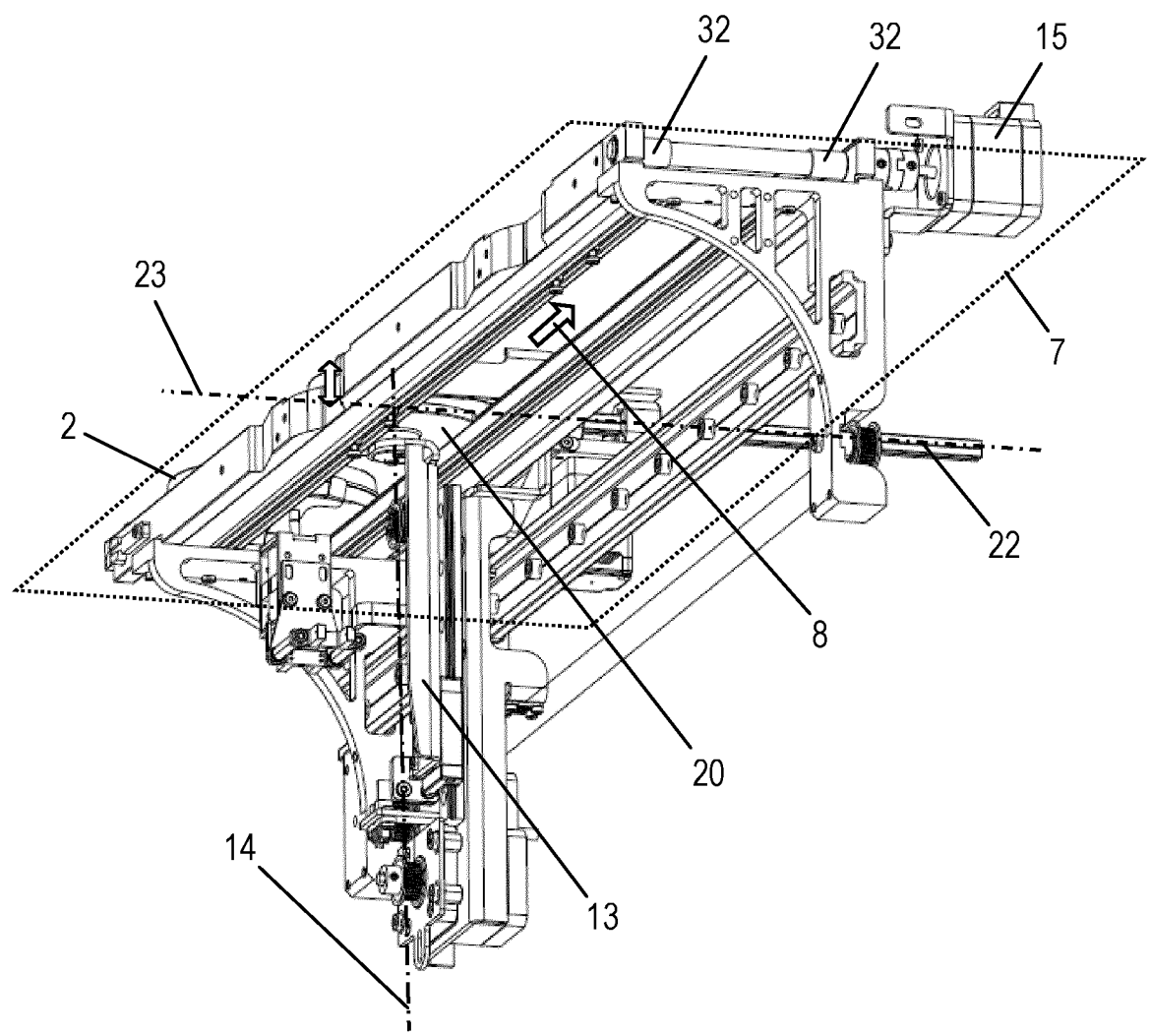
FIG. 4 shows in a perspective view from below the part of the system of FIG. 2.

The first elevator 13, which is shown in more detail in FIGS. 3 and 4, comprises a substantially flat first plate 20, which is built to receive the petri dishes 2, for example simply by moving or pushing them onto the first plate 20. "Substantially flat" in this context means that the petri dish 2 can be moved or pushed onto the first plate 20, for example by pushing means or by another petri dish 2, without any appreciable resistance from the first plate 20, wherein the first plate 20 needs to be in a first neutral position located in the conveyor plane 7, as shown in FIG. 3. In addition, the first elevator 13 comprises pushing means 22, which are built to move the petri dish 2 on the conveyor plane 7 along a pushing axis 23 substantially transversal to the conveyor direction 8. The first elevator 13 may comprise a sensor, for example a position or a weight sensor in order to detect the petri dish 2 being received by the first plate 20.

The second elevator 24 comprises a substantially flat second plate 26, which is built to receive the petri dishes 2, for example simply by moving or pushing them onto the second plate 26. "Substantially flat" in this context means that the petri dish 2 can be moved or pushed onto the second plate 26, for example by the pushing means 22 of the first elevator 13, without any appreciable resistance from the second plate 26, wherein the second plate 26 needs to be in a second neutral position located in the conveyor plane 7, as shown in FIG. 2. In addition, the second elevator 24 comprises a sensor 27 built to communicate with the control unit 11 and to detect the petri dish 2 on the second plate 26.

Advantageously, the form of the first plate 20 and the second plate 26 is circular or of a segment of a circle.

The control unit 11 is built to move the first elevator 13 along the conveyor direction 8 of the conveyor 6. Carrier positions 18 are virtually situated at the points of intersection of the carrier axes 17 with the conveyor plane 7. If the petri dish 2 is to be sorted into one of the carriers 12, in case of a first information assigned to the petri dish 2 the first elevator 13 is moved to one of these carrier positions 18, which is reached as soon as the respective carrier axis 17 and the first elevator axis 14 substantially coincide. Subsequently, the control unit 11 moves the first plate 20 with the petri dish 2 along the first elevator axis 14 from the first neutral position into a first transfer position, which is reached as soon as the petri dish 2 is being taken over by the respective carrier 12. Advantageously, the carriers 12 are directly situated above the conveyor 6, as shown in FIG. 2, so that, in an installation orientation of the system 1, the control unit 11 can simply move the first elevator 13, and consequently the first plate 20, upwards along the first elevator axis 14 from the first neutral position into the first transfer position.

"Installation orientation" denotes the customary spatial orientation or spatial situation of the system 1 or the processing apparatus 31 within its processing or working environment after its installation. The customary installation orientation of the system 1 or the processing apparatus 31 is such that the conveyor plane is substantially horizontal and that the multi-carrier axes 9, the second elevator axis 25, the first elevator axis 14 and the carrier axis 17 are substantially vertical. Of course, the system 1 or the processing apparatus 31 according to the invention are not limited to such an installation orientation.

"The petri dish 2 is being taken over by one of the carriers 12" in this context means that the petri dish 2 is being moved or pushed into the carrier 12 by the first plate 20, and that the carrier 12 holds the weight of the petri dish 2, so that the first plate 20 can be moved back into its first neutral position without carrying the petri dish 2 any longer. This take-over of the petri dish 2 by the carrier 12 can for example be realized by one-way hinges 19 that are tiltable into the movement direction of the first plate 20 from the first neutral position into the first transfer position, and non-tiltable against the movement direction of the first plate 20 from the first transfer position into the first neutral position. Alternatively, the hinges can be retractable controlled by the control unit 11 in order to retract the hinges during movement of the petri dish 2 into the carrier 12 and to extend the hinges as soon as the petri dish 2 has been taken over by the carrier 12. Those skilled in the art will be aware of the fact that other technical solutions of such a take-over may be used.

Besides the carrier positions 18, there are multi-carrier positions 21 virtually situated along the conveyor 6. In case of a second information assigned to the petri dish 2, the petri dish 2 is to be sorted into one of the multi-carriers 5. Consequently, the first elevator 13 is moved into one of these multi-carrier positions 21, which is reached as soon as a centre of the second plate 26 lies on the pushing axis 23 of the pushing means 22 of the first elevator 13. Subsequently, the control unit 11 controls the pushing means 22 to move the petri dish 2 along the pushing axis 23 onto the second plate 26 of the second elevator 24. As soon as the sensor 27 identifies the petri dish 2, the control unit 11 moves the second plate 26 with the petri dish 2 along the second elevator axis 25 in the extent of the height of the petri dish 2 from the second neutral position downwards into a second transfer position, which is reached as soon as the bottom container of the petri dish 2 levels with the conveyor plane 7. Thus, a next or new petri dish 2 can be easily moved onto the petri dish 2 by the pushing means 22.

If the second plate 26 already carries one or more prior petri dishes 2, the control unit 11 controls the pushing means 22 to move the new petri dish 2 along the pushing axis 23 onto the upmost of the petri dishes 2 carried by the second plate 26. As soon as the sensor 27 identifies the new petri dish 2, the control unit 11 moves the second plate 26 with the petri dishes 2 along the second elevator axis 25 in the extent of the height of the new petri dish 2 from the prior second transfer position into a new second transfer position, which is reached as soon as the bottom container of the new petri dish 2 levels with the conveyor plane 7.

Thus, with each petri dish 2 to be sorted into the multi-carrier 5 the second plate 26 is moved downwards in the extent of the height the petri dish 2, from its current second neutral position into an new second transfer position. Thus, each petri dish 2 can be easily moved onto the recent upmost petri dish 2 by the pushing means 22. This procedure can be repeated until the current multi-carrier axis 9 is full. If the current multi-carrier axis 9 is full, the second plate 26 lowers the petri dishes 2 onto the multi-carrier 5 and the platform 28 can be rotated in order to position a new, "empty" multi-carrier axis 9 in accordance to the second elevator axis 25. Subsequently, the control unit 11 moves the second plate 26 into the second neutral position in order to receive the next petri dish 2.

As shown in FIG. 2, each multi-carrier 5 is situated below the conveyor plane 7. Thus, in an installation orientation of the system 1, the control unit 11 can simply move the second elevator 24 downwards along the second elevator axis 25 from the second neutral position into the second transfer positions. Thus, the carriers 12 and the multi-carriers 5 are clearly spatially separated, which improves the sorting effect and reduces the error-proneness of the system 1.

A partially full or completely full carrier 12 or multi-carrier 5 may be simply automatically or manually removed from the system 1 and replaced by a new empty carrier 12 or multi-carrier 5.

Summarizing, a method for a fast automated analyzing and sorting process of a high number of petri dishes 2 according to the invention may be accomplished by processing the following steps:

The analysis tool 3 analyses the petri dish 2 and assigns information to the petri dish 2, for example information regarding an analysis result, and communicates this information to the control unit 11.

Pushing means or a second succeeding petri dish 2 move/s the petri dish 2 along the conveyor direction 8 onto the first plate 20 of the first elevator 13.

According to the assigned information of the petri dish 2, in case of the first information assigned to the petri dish 2 the control unit 11 moves the first elevator 13 along the conveyor direction 8 into the carrier position 18 and, as soon as the first elevator 13 reaches the carrier position 18, the control unit 11 moves the first plate 20 along the first elevator axis 14 from the first neutral position located in the conveyor plane 7 into the first transfer position, wherein the carrier 12 takes over the petri dish 2, or in case of the second information assigned to the petri dish 2 the control unit 11 moves the first elevator 13 into a multi-carrier position 21, and, as soon as the first elevator 13 reaches the multi-carrier position 21, the control unit 11 moves the petri dish 2 via the pushing means 22 along the pushing axis 23 onto the second plate 26, and the control unit 11 moves the second plate 26 along the second elevator axis 25 from the second neutral position located in the conveyor plane 7 into the second transfer position, which is reached as soon as the bottom container of the upmost petri dish 2 carried by the second plate 26 levels with the conveyor plane 7.

A system 1 according to a further embodiment of the invention could be adopted to handle and/or sort petri dishes 2 within, to or from analysis tools or equipment, such as a chemical composition analysis tool, an incubation system, an oven, a storage system, a sorting system, a weighting tool, radiation equipment such as X-Ray, IR or UV, labelling equipment in order to label the petri dishes 2, or similar systems.

A system according to a further embodiment of the invention could be adopted to handle and/or sort petri dishes of rectangular or quadratic form, involving a rectangular or quadratic bottom container and a rectangular or quadratic lid. In this case, the lid diameter is the diagonal of the rectangular or quadratic lid. Additionally the petri dishes could be of any random form, involving a bottom container having advantageously substantially the same form as the lid.

A system according to a further embodiment of the invention could be adopted to sort all kinds of similar flat and transparent or non-transparent containers or boxes with a lid, such as laboratory ware or boxes/containers containing chemical or biological material or electronic devices.

The invention claimed is:

1. A system for analyzing and sorting of petri dishes comprising an analysis tool, a control unit configured to communicate with the analysis tool, a first elevator movable along a first elevator axis by the control unit, a conveyor with a conveyor plane substantially rectangular to the first elevator axis, and at least one carrier configured to carry the petri dishes along a carrier axis substantially parallel to the first elevator axis, wherein the analysis tool is configured to analyse the petri dish and to assign information to the petri dish based upon the analysis, the control unit is configured to move the first elevator along a conveyor direction of the conveyor and to move the petri dish by means of the conveyor on the conveyor plane along the conveyor direction from the analysis tool toward a first neutral position for sorting, and in case of information assigned to the petri dish is a first information, the control unit is configured to move the first elevator into a carrier position, which is virtually situated at the point of intersection of the carrier axis with the conveyor plane and reached as soon as the carrier axis and the first elevator axis substantially coincide, wherein, as soon as the first elevator reaches the carrier position, the control unit is configured to move a substantially flat first plate of the first elevator along the first elevator axis, which first plate is configured to receive the petri dish from the conveyor, to move the first plate from the first neutral position located in the conveyor plane into a first transfer position according to the first information, which is reached as soon as the petri dish is being taken over by the at least one carrier.

2. The system according to claim 1, wherein in an installation orientation of the system, as soon as the first elevator reaches the carrier position, the control unit is configured to move the first plate along the first elevator axis in order to move the first plate from the first neutral position upwards into the first transfer position.

3. The system according to claim 1, wherein the first elevator comprises pushing means configured to move the petri dish on the conveyor plane along a pushing axis substantially transversal to the conveyor direction.

4. The system according to claim 3, wherein in case information assigned to the petri dish is a second information, the control unit is configured to move the first elevator into a multi-carrier position, which is reached as soon as a centre of a second plate of a second elevator lies on the pushing axis of the pushing means of the first elevator, wherein, as soon as the first elevator reaches the multi-carrier position, the control unit is configured to control the pushing means to move the petri dish along the pushing axis onto the second plate or onto an upmost petri dish carried by the second plate, which second plate is movable along a second elevator axis by the control unit.

5. The system according to claim 4, wherein the second elevator comprises a sensor configured to communicate with the control unit and to detect the petri dish on the second plate.

6. The system according to claim 4, comprising at least one multi-carrier configured to carry the petri dishes along at least two multi-carrier axes substantially parallel to the second elevator axis, wherein one multi-carrier axis substantially coincides with the second elevator axis.

7. The system according to claim 6, wherein in the installation orientation of the system, the control unit is configured to move the second plate along the second elevator axis from a second neutral position located in the conveyor plane downwards into second transfer positions, which are reached each time a bottom container of the upmost petri dish carried by the second plate levels with the conveyor plane.

8. The system according to claim 6, wherein the at least one multi-carrier is configured to carry the petri dishes along four multi-carrier axes.

9. The system according to claim 6, comprising at least one rotatable platform configured to receive the at least one multi-carrier, wherein the rotatable platform is rotatable around a platform axis by the control unit in order to position the at least two multi-carrier axes in accordance to the second elevator axis.

10. The system according to claim 1 comprising a carrier sensor system configured to communicate with the control unit and to detect the petri dishes carried by the at least one carrier.

11. The system according to claim 1, wherein the conveyor is realized as a conveyor belt driven by a conveyor drive, wherein the conveyor belt is split into two conveyor belts separated by a gap.

12. A method for analyzing and sorting of petri dishes with a system comprising an analysis tool, a control unit, a first elevator movable along a first elevator axis, a conveyor, and at least one carrier and at least one multi-carrier, respectively configured to carry the petri dishes, wherein the following steps are processed:
 analyse and assign information to the petri dish with the analysis tool, based upon the analysis, and communicate this information to the control unit;
 move the petri dish by means of the conveyor on a conveyor plane along a conveyor direction from the analysis tool toward a first neutral position for sorting;
 receive the petri dish from the conveyor on a substantially flat first plate of the first elevator;
 in case information assigned to the petri dish is a first information, move the first elevator along the conveyor direction of the conveyor into a carrier position virtually situated at the point of intersection of a carrier axis with the conveyor plane and, as soon as the first elevator reaches the carrier position, move the first plate along the first elevator axis from the first neutral position into a first transfer position, and take over the petri dish by the carrier.

13. The method according to claim 12, wherein, in an installation orientation of the system, in case of the first information assigned to the petri dish the first plate is moved along the first elevator axis from the first neutral position upwards into the first transfer position.

14. The method according to claim 12, wherein in case information assigned to the petri dish is a second information, the first elevator is moved along the conveyor direction of the conveyor into a multi-carrier position and, as soon as the first elevator reaches the multi-carrier position, the petri dish is moved via pushing means along a pushing axis substantially transversal to the conveyor direction onto a second plate of a second elevator, which second plate is movable along a second elevator axis, or onto an upmost petri dish carried by the second plate.

15. The method according to claim 14, wherein, in the installation orientation of the system, in case information assigned to the petri dish is a second information, the second plate is moved along the second elevator axis from a second neutral position downwards into a second transfer position.

* * * * *